(12) United States Patent
Müller et al.

(10) Patent No.: US 6,814,959 B1
(45) Date of Patent: Nov. 9, 2004

(54) UV RADIATION REFLECTING OR ABSORBING AGENTS, PROTECTING AGAINST HARMFUL UV RADIATION AND REINFORCING THE NATURAL SKIN BARRIER

(75) Inventors: Rainer H. Müller, Berlin (DE); Sylvia Wissing, Berlin (DE); Karsten Mäder, Berlin (DE)

(73) Assignee: PharmaSol GmbH, Berlin (DE)

( * ) Notice: Subject to any disclaimer, the term of this patent is extended or adjusted under 35 U.S.C. 154(b) by 0 days.

(21) Appl. No.: 10/030,425

(22) PCT Filed: Jul. 10, 2000

(86) PCT No.: PCT/EP00/06534
§ 371 (c)(1),
(2), (4) Date: Apr. 8, 2002

(87) PCT Pub. No.: WO01/03652
PCT Pub. Date: Jan. 18, 2001

(30) Foreign Application Priority Data

Jul. 13, 1999 (DE) .......................................... 199 32 156
Mar. 31, 2000 (DE) .......................................... 100 16 155

(51) Int. Cl.⁷ ............................. A61K 7/42; A61K 7/44; A61K 31/74; A61K 7/00

(52) U.S. Cl. ...................... 424/59; 424/60; 424/78.02; 424/78.08; 424/400; 424/401

(58) Field of Search ............................ 424/59, 60, 400, 424/401, 78.02, 78.08

(56) References Cited

U.S. PATENT DOCUMENTS

| | | | |
|---|---|---|---|
| 5,496,565 A | 3/1996 | Heinze et al. | |
| 5,733,531 A | 3/1998 | Mitchnick et al. | |
| 5,904,932 A | 5/1999 | De Vringer | |

FOREIGN PATENT DOCUMENTS

| | | |
|---|---|---|
| DE | A61K9/127 | 3/1993 |
| EP | 0 379 409 | 7/1990 |
| EP | 0 529 396 | 3/1993 |
| EP | 0 573 229 | 12/1993 |
| WO | WO 98/46200 | 10/1998 |
| WO | WO 00/67728 | 11/2000 |

Primary Examiner—Shelley A. Dodson
(74) Attorney, Agent, or Firm—Jeffrey S. Melcher; Manelli Denison & Selter, PLLC

(57) ABSTRACT

The invention relates to agents with UV radiation-absorbing and/or reflecting action comprising solid, polymorphic, crystal-line or partially crystalline lipid and/or polymer particles, for application to the skin, mucous membranes, scalp, and hair for protection against health-damaging UV radiation and for strengthening the natural skin barrier.

41 Claims, 10 Drawing Sheets

Figure 1:
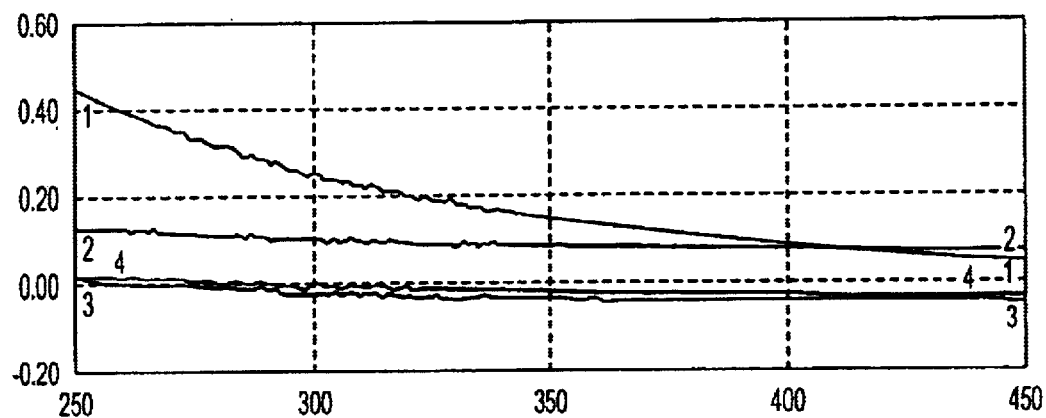

UV RADIATION REFLECTING OR ABSORBING AGENTS, PROTECTING AGAINST HARMFUL UV RADIATION AND REINFORCING THE NATURAL SKIN BARRIER

The invention relates to solid agents, comprising polymorphic lipid particles, with UV radiation-absorbing and/or reflecting action for application on the skin, mucous membranes, scalp and hair for protection against health-damaging UV radiation and for strengthening the natural skin barrier.

With the increase in the ozone hole and the worldwide decrease in the thickness of, the ozone layer and the resultant increasing exposure of the human skin to health-damaging UV radiation, there is an increasing need and necessity for agents which protect the skin from UV radiation, that is, which weaken or, ideally, completely block the UV radiation. The health-damaging effect of UV rays makes itself apparent in the form of skin cancer (e.g. melanoma), among other things. The increase in UV radiation load on the skin in recent years has led to a great increase in skin cancers. Whereas the incidence of some cancer types is declining, melanoma of the skin is one of the cancer types with the highest rate of increase, as a result of the increasing UV load. New cases of malignant melanoma are doubling every 5 years (E. Wolf, Angst vor der Sonne, Pharmazeutische Zeitung 144, 1839–1843). The population of countries with high and intensive exposure to the sun is affected in particular, e.g. ozone hole above South Chile, New Zealand and Australia. Thus, the incidence of malignant melanoma in Australia is five times higher than in Central Europe (E. Wolf, Angst vor der Sonne, Pharmazeutische Zeitung 144, 1839–1843).

The traditional approach to providing protection from UV radiation is the incorporation of molecules which absorb UV radiation (so-called UV blockers) in creams or lotions which are applied to the skin as protection against the sun and remain there for hours. (N. J. Lowe, Photoprotection, Seminars in Dermatology, Vol. 9, NO. 1, 1990, 78–83). Strictly speaking, the term "UV blocker" is misleading, as the UV radiation is not completely blocked, but only lessened to a greater or lesser extent, depending on the concentration and chemical nature of the substances which are used.

One of the disadvantages of the molecular UV blockers is that, analogously to drugs incorporated into cream, they diffuse into the skin. This is desired with drugs but not with UV blockers, as they cause unwelcome side-effects.

Side-effects of UV blockers are e.g. photosensitization such as photoallergy and phototoxicity, and skin irritations. With sensitive persons, a foreign substance—often a topical chemical UV filter—is activated by UV radiation and this activated form then causes this reaction (E. Wolf, Angst vor der Sonne Pharmazeutische Zeitung 144, 1839–1843). With some substance classes (salicylides), skin irritations are so marked that they cannot be applied to the skin. This has resulted in the requirement to minimize penetration into the skin (E. Mariani, C. Neuhoff, A. Bargagna, F. Bonina, M. Giacchi, G. De Guidi, A. Velardita, Synthesis, in vitro percutaneous absorption and phototoxicity of new benzylidene derivatives of 1,3,3-trimethyl-2-oxabicyclo (2,2,2) octan-6-6-one as potential UV sunscreens, Int. J. Pharm. 161, 65–73). With good solubility in the vehicle (e.g. molecular UV blockers in the oil phase of a lotion or cream), a penetration into the skin can however come about very easily. (U. Hagedorn-Leweke, B. C. Lippold, Accumulation of sunscreens and other compounds in keratinous substrates, Eur. J. Pharm. Biopharm. 46, 215–221). The skin penetration of molecular UV blockers is thus an unsolved problem. Hence the stronger call to employ physically acting light filters which do not penetrate the skin (E. Wolf, Angst vor der Sonne, Pharmazeutische Zeitung 144, 1839–1843).

A further problem is that toxicological testing of UV blockers is in accordance with the guidelines for cosmetics, which are less strict than those for drug tests. UV blockers can decompose under the action of UV radiation. Reactive decomposition substances thus form which can be toxicologically problematical, especially where there is skin penetration. It is known of some UV blockers that they specifically bond to keratin structures of the skin and can therefore be washed off only with difficulty (U. Hagedorn-Leweke, B. C. Lippold, Accumulation of sunscreens and other compounds in keratinous substrates, Eur. J. Pharm. Biopharm. 46, 215–221). To minimize toxicity, an ideal sunscreen should be removable by washing after sunbathing.

The penetration—and therefore the side effects—can be particularly marked if the UV blockers are dissolved in the aqueous phase of oil-in-water (O/W) creams or lotions. The phase in direct contact with the skin (water phase) has a high concentration of UV blockers so that the water phase-to-skin concentration gradient is high, which, according to Fick's first law of diffusion, promotes penetration into the skin. This is an effect which is selectively exploited in pharmacy with transdermal therapeutic patches, but which is undesirable, and must be minimized, with UV blockers.

One approach to minimizing skin penetration is the use of lipophilic UV blockers with low water-solubility. These are dissolved in the oil phase of the cream or lotion. The water phase contains a much lower concentration of UV blockers. With a favourable chemical structure of the UV blocker, this can slow down penetration into the skin as a result of the concentration gradient now being smaller, but does not avoid it. UV blocker diffused out of the wtaer phase into the skin is replaced by the diffusion of further UV blocker out of the oil phase into the water phase. The redistribution into the water phase takes place according to the Nernst's distribution coefficient of a substance.

To avoid the side effect of molecular UV blockers, the approach of using particulate UV blockers has been followed. An example is the widely used inorganic titanium dioxide (B. L. Diffey, P. M. Farr, Sunscreen protection against UVB, UVA and blue light; an in vivo and in vitro comparison, British Journal of Dermatology 124, 1991, 258–263). The basic idea was that the particles, by virtue of their size, do not diffuse into the skin and thus should not cause any side-effects. After sunbathing, the particles should be washed off the skin by normal body cleaning (e.g. shower).

Particulate UV blockers such as micropigments (e.g. titanium dioxide) have an immediately, conspicuous cosmetic disadvantage in preparations with a high light-protection factor. With the necessary large amount of pigment, a whitening effect occurs (E. Wolf, Angst vor der Sonne, Pharmazeutische Zeitung 144, 1839–1843). Very small titanium dioxide particles have proven to be particularly effective (B. L. Diffey, P. M. Farr, Sunscreen protection against UVB, UVA and blue light; an in vivo and in vitro comparison, British Journal of Dermatology 124, 1991, 258–263), so that they have accordingly been used at concentrations of up to 25% in cosmetics. However, interactions and side-effects with the skin have also bee n found with titanium dioxide particles (R. G. van der Molen et al, Efficacy of micronized titanium dioxide-containing compounds in protection against UVB-induced immunosuppression in humans in vivo, Journal of Photochemistry and Photobiology 44, 2, 1998, 143–150), and it can no longer be ruled out that titanium dioxide penetrates the skin (R. G. van der Molen, Tape stripping of human stratum corneum yields cell layers that originate from various depths because of furrows in the skin, Archives of Dermatological Research, 289, 9, 1997, 514–518). Thus it has been shown for example, that titanium dioxide can photocatalyze the formation of free radicals (W. G. Warner, Oxidative damage to nucleic acids photosensitized by titanium dioxide, Free Radical Biology and medicine, 23, 6, 1997, 851–858), which is to be viewed critically both in the skin and on the skin and also during storage.

In summary it can thus be established that, in view of the more intensive radiation load, with a simultaneous increase in use, a need exists both for more efficient and toxicologically better compatible sunscreens, especially also for highly sensitive areas of the skin.

The object of the invention is to provide a better compatible agent for protection against harmful UV radiation which avoids the disadvantages described above and, in particular, greatly minimizes or avoids the redistribution of UV blockers from the dispersion phase (e.g. oil drops of a lotion) into the outer (dispersed) phase.

According to the invention, to achieve the object, the liquid lipids customarily used until now, from which molecules can easily diffuse, have been replaced by solid lipid and/or polymer in the form of solid, polymorphic, crystalline or partly crystalline lipid- and/or polymer particles of a size below 100 $\mu$m (average size of the main population), which are characterized in that during the heating-up phase in thermal calorimetry (DSC Differential Scanning Calorimetry) above 20° C. an endothermic peak is to be observed. Depending on requirements, UV blockers are incorporated into the solid lipid- and/or polymer particles. Sunscreens produced in this way are no longer emulsions, but technically constitute a suspension.

The expression "polymorphic" refers to the property of molecules of being able to exist in different modifications. The polymorphic forms can be crystalline (fully crystalline) (e.g. $\beta$-, $\beta$i-modifications) or liquid-crystalline (e.g. $\alpha$-modification). When there are several different modifications (crystalline and liquid-crystalline), a partially crystalline form of the particles according to the invention can therefore also result. If only modifications with crystalline structure are present, the particles are also crystalline. If both regions with modifications with a crystalline structure and regions with a liquid-crystalline structure are present in the particles according to the invention, the particles are partially crystalline overall.

The stated particle sizes are the average of the main population. With small particles, it is the average diameters measured by photon correlation spectroscopy (PCS, measurement range 3 nm to 3 $\mu$m) or laser diffractometry (LD). In the case of particles of >3 $\mu$m, it is average diameters measured by laser diffractometry. Unless specified otherwise, it is the 50% LD diameter.

In the following, for the sake of simplicity, the invention is describe with reference to versions (a) which include lipids According to the invention, however, also included are versions (b) which include polymers, or versions (c) which contain lipids and polymers. Therefore, the explanations also apply to these alternative versions.

In ascertaining the UV-blocking action, it was surprisingly found that, compared with emulsions, the lipid particles already have a blocking action against UV radiation even without incorporated molecular UV blocker (Examples 1–3). This thus even opens up the possibility of dispensing with toxicologically unfavourable molecular UV blockers.

The UV-blocking action of the solid lipid particles decreases as the concentration increases, so that the desired light-protection factor can be set via the particle concentration (Example 4).

The UV-blocking action is also a function of particle size. Lipid nanoparticles, with identical lipid concentration in the suspension, were more effective than microparticles measuring 4.6 $\mu$m (Example 5). This was confirmed by tests on polymer particles of varying size. Particles in the range of approx. 500 nm to 1000 nm showed the strongest UV-blocking action; very small nanoparticles (60 nm) and larger microparticles were leas effective (Example 7).

The data show that, in principle, polymer particles can be used as UV blockers, analogously to lipid microparticles. However, a disadvantage here is that inexpensive polymers such as polystyrene, poly(meth)acrylates, polycarbonates, polyamides or polyurethanes are not, or only slowly, degradable, and would heavily pollute the environment if used on a large scale in sunscreens. Biologically degradable polymers such as polyhydroxybutyric acid or polyhydroxyvaleric acid or polylactides are however, comparatively more expensive, which possibly limits their use in relatively low-priced sunscreens.

Polymer particles with a UV-blocking action can be prepared from various, chemically very different polymers. However, generally suitable as polymers are polymers which are solid at room temperature (20° C.) such as polystyrene, polyacrylates, polymethacrylates, polycarbonates, polyamides, polyurethanes, polyhydroxybutyric acid (PHB), polyhydroxyvaleric acid (PHV), celluloses und cellulose derivatives, in particular cellulose hydrates, polylactides (PLAs), polyglycolide (PPGAs) and their copolymers (PLAs/GAs) individually or in a mixture. Mixtures of lipids and polymers can also be used.

However, lipid microparticles are ecologically most advantageous, especially if they are manufactured from renewable raw materials (e.g. vegetable lipids); at the same time, they are the most cost-favourable in economic terms.

The lipid particle suspension can be applied directly to the skin; if desired, a gelation agent can be added to increase viscosity. Alternatively, the particles can also be incorporated into lotions and creams. They are physically stable in them and do not dissolve in the oil phase (Example 6).

After being spread on a surface, the lipid particles form uniform films, a requirement for an effective UV-blocking action (Example 8). Perforated, porous films did not result, as feared, but instead the formation of a sealed film (Example 18). This lipid film strengthens the natural skin barrier, especially if a damaged natural lipid film is already present on the stratum corneum.

UV blockers can also be incorporated into the lipid particles in order to additionally increase the UV-blocking action (Examples 11 and 12). Surprisingly, it was discovered that the effect of lipid particles and UV blockers can be not only additive, but also synergistic (Example 17).

As exposure to the sun can mean stress for the skin, it can be advisable to incorporate skin-care substances, such as retinol palmitate or antioxidants such as tocopherol, into the lipid particles. Both active substance groups can also be processed simultaneously.

The lipid particles according to the invention can also be used to minimize the interaction of inorganic or organic pigments with the skin. Analogously to the molecular UV blockers, the pigments (pigmentary or particulate UV blockers) are enclosed in the solid lipid matrix. The enclosure can also take place without problems in lipid particles in the lower nanometer range (e.g. 200 nm particles), as many pigments are very small (approx. 10–40 nm with magnesium layer silicates such as Aerosil, approx. 15–20 nm in the case of titanium dioxide) (Examples 15 and 16).

It is also possible to incorporate a combination of molecular UV blockers and particulate UV blockers (pigments) as well as simultaneously add skin-care active substances as well as antioxidants, either into the solid lipid matrix or to the outer phase of the lipid particle dispersion.

The lipid particle dispersions according to the invention can also be manufactured free of emulsifiers, which is important for the avoidance of Mallorca acne. Mallorca acne is not triggered by UV-A radiation alone, but by its interaction with emulsifiers in cosmetics (E. Wolf, Angst vor der Sonne, Pharmazeutische Zeitung 144, 1839–1843).

Additionally, there are possible applications on the scalp and hair (e.g. to avoid sunburn with thin hair, avoidance of bleaching effects on hair). Particularly to increase the adhesion to negatively charged hair, the lipid particles can be produced with a positive charge by using suitable surfactants.

To increase acceptance of the UV absorption agent, natural, synthetic or semi-synthetic fragrances can be incorporated into the lipid particles, e.g. perfumes, ethereal oils or pheromones.

Examples of perfumes are Allure, Coco, Egoiste, Chanel No. 5, 19, 22 from Chanel, Miss Dior, Dune, Diorissime or Fahrenheit from Dior, Roma, Laura, Venezia from Laura Biagotti, L'air du temps from Nina Ricci, Chalimar from Guerlain, Tresor from Lancome, Gio from Armani, Escape, Obsession, CK One, CK be, Eternity from Calvin Klein, Berlin, Joop, Rococo, All about Eve, What about Adam, Nightflight from Joop, KL, Lagerfeld, Jako from Karl Lagerfeld, Extreme from Bulgari.

Examples of ethereal oils are lemon oil, rose oil, lavender oil, bergamot oil, balm mint oil, clove oil, cinnamon oil, orange oil, jasmine oil, rosemary oil, aniseed oil, peppermint oil, sandal wood oil, ylang-ylang oil or their isolated ingredients such as e.g. 1,8-cineole, menthol, terpinol hydrate, limonene, α-pinene, eugenol.

Examples of pheromones are in particular, human pheromones such as androstenone or androstenol.

The scents can be incorporated into the lipid particles alone or in combination with, for instance, UV blockers such as e.g. particulate or molecular UV blockers.

To use the agent for UV absorption in areas plagued by insects, (e.g. mosquitoes on Indian beaches), repellents can be incorporated into the lipid particles. Examples of repellents are natural repellents such as citrus oils, eucalyptus oil und camphor or synthetic repellents such as N,N-diethyl-toluamide (DEET), dibutyl phthalate, dimethyl phthalate, 2-ethyl-1,3-hexanediol.

The repellents can be incorporated into the lipid particles alone or in combination with scents and/or UV blockers such as e.g. particulate or molecular UV blockers.

The invention is described in more detail in the following with the help of the attached FIGS. 1 to 18 and examples.

In each of FIGS. 1–5 and 7–17, the wavelength [nm] is plotted on the abscissa and the absorption values on the ordinate.

FIG. 1: Spectrophotometric scans of aqueous dispersions (Example 1) Cetyl palmitate—Tego Care, (2) Miglyol—Tego Care, (3) Cetyl palmitate, (4) Tego Care FIG. 2: Spectophotometric scans of aqueous dispersions (Example 2) Stearyl alcohol—Tween 80, (2) Miglyol—Tween 80, (3) Stearyl alcohol, (4) Tween 80

Figure 3:
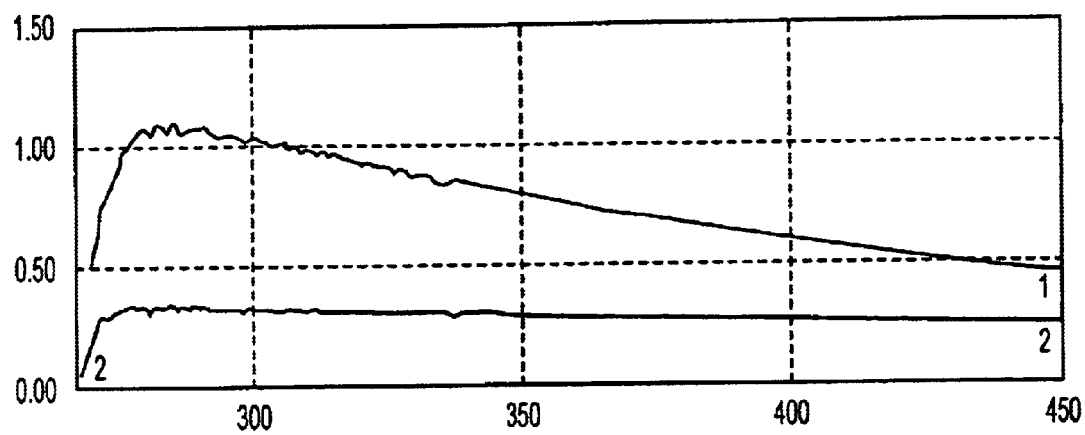

FIG. 3: Spectrophotometric scans of lipid films (Example 3) Cetyl palmitate—Tego Care, (2) Miglyol—Tego Care FIG. 4: Spectrophotometric scans of lipid films (Example 4) 10% cetyl palmitate, (2) 20% cetyl palmitate, (3) 30% cetyl palmitate, (4) 40% cetyl palmitate FIG. 5: Spectrophotometric scans of lipid films (Example 5) Nanoparticles (d50% 138 nm), (2) Micropartic-les (d50% 4.6 μm)

Figure 6:
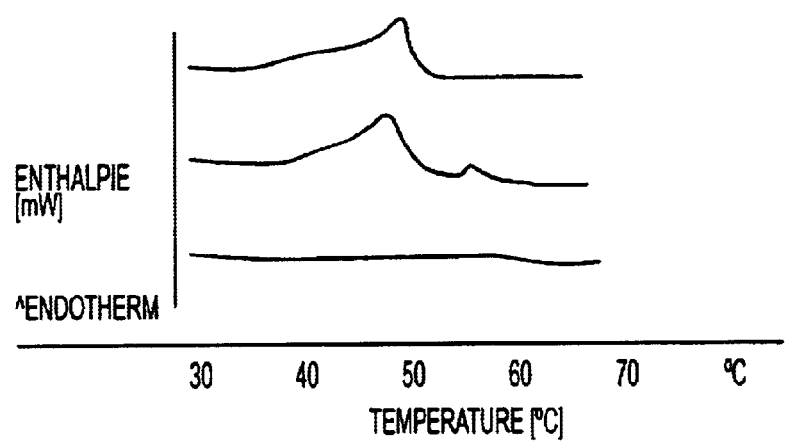

FIG. 6: Thermogram of a cetyl palmitate SLN dispersion (top) in comparison with the dispersion incorporated into a O/W-cream (middle) (standardized on the proportion of SLN-dispersion as well as the pure O/W-cream without SLN (bottom))

Figure 7:
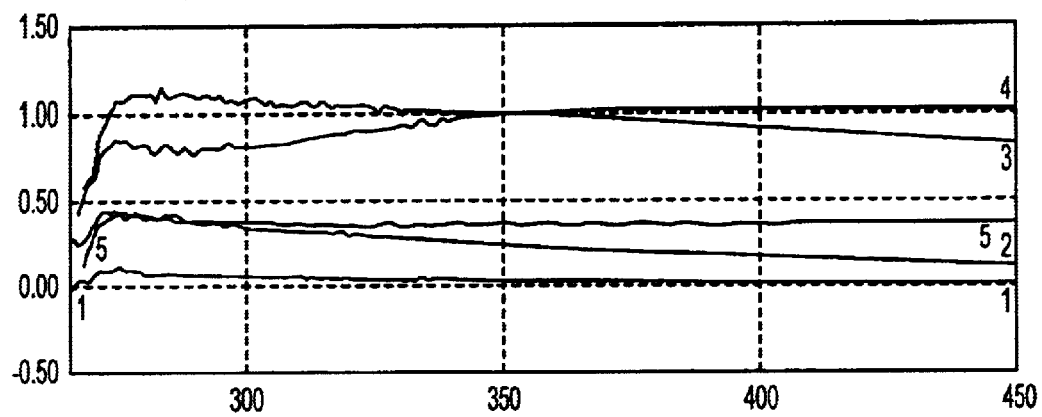

FIG. 7: Spectrophotometric scans of polystyrene particle films (Example 7) 60 nm, (2) 100 nm, (3) 528 nm, (4) 949 nm, (5) 3000 nm FIG. 8: Spectrophotometric scans of lipid films for determining film uniformity (Example 8) (1)–(6) different positions of the cuvette in the holder FIG. 9: Spectrophotometric scans of lipid films Fill (example 9), cetyl palmitate—Tego Care—Eusolex 4360, (2) cetyl palmitate—Tego Care FIG. 10: Spectrophotometric scans of lipid films (Example 10) 10% Eusolex 4360, (2) 5% Eusolex 4360, (3) 1% Eusolex 4360

Figure 11:
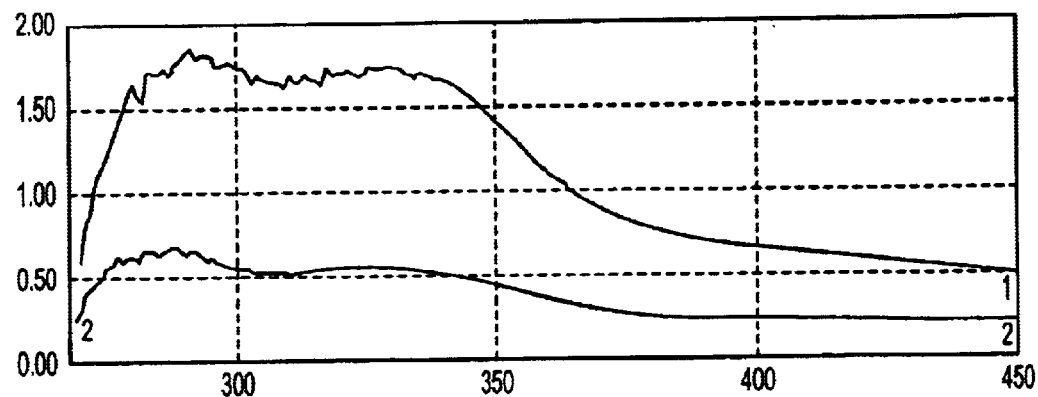

FIG. 11: Spectrophotometric scans of lipid films (Example 11) cetyl palmitate—Tego Care—Eusolex 4360, (2) Miglyol—Tego Care—Eusolex 4360

Figure 12:
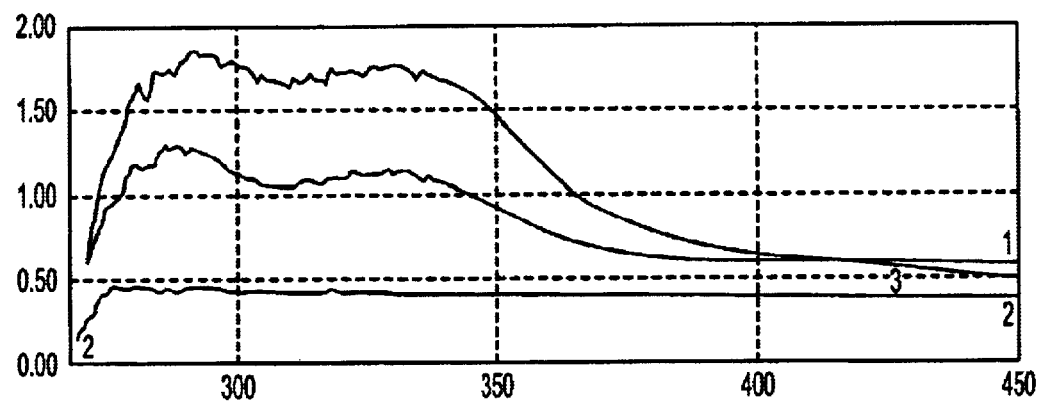

FIG. 12: Spectrophotometric scans of lipid films (Example 12) micrometer particles with Eusolex 4360 (d50% 12 μm), (2) micrometer particles (d50% 4.6 μm), (3) nanometer particles with Eusolex 4360 (d50% (2) 138 nm)

Figure 13:
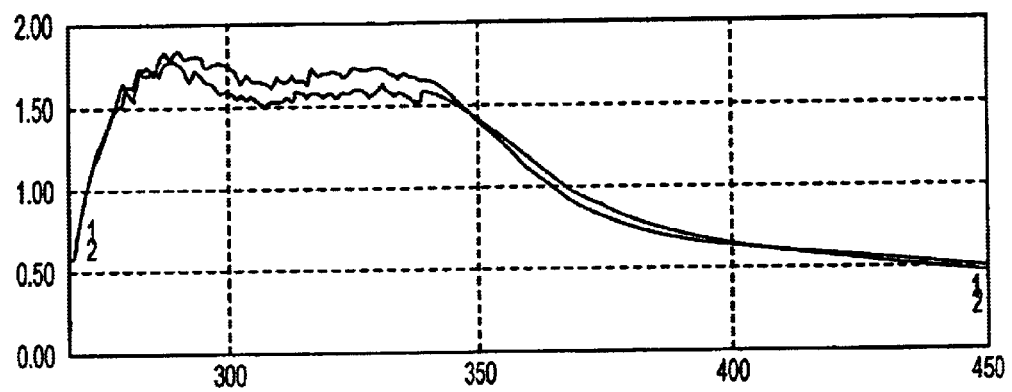

FIG. 13: Spectrophotometric scans of lipid films (Example 13) cetyl palmitate—Tego Care—Eusolex 4360—vitamin A palmitate, cetyl palmitate—Tego Care—Eusolex 4360

Figure 14:
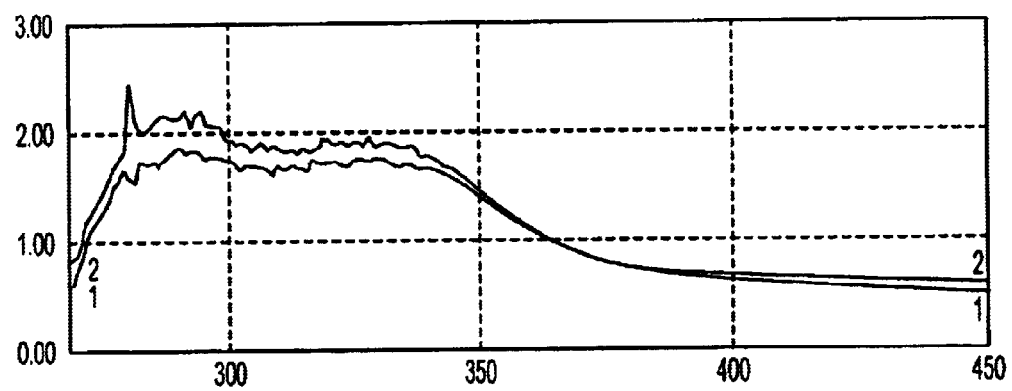

FIG. 14: Spectrophotometric scans of lipid films (Example 14) cetyl palmitate—Tego Care—Eusolex 4360—vitamin E, cetyl palmitate—Tego Care—Eusolex 4360

Figure 15:
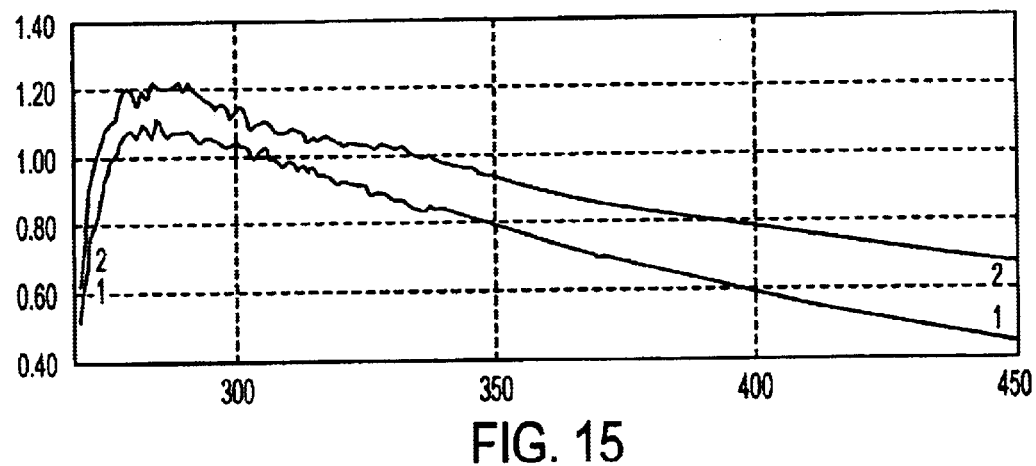

FIG. 15: Spectrophotometric scans of lipid films (Example 15) cetyl palmitate—Tego Care, (2) cetyl palmitate—Tego Care—Aerosil 200

Figure 16:
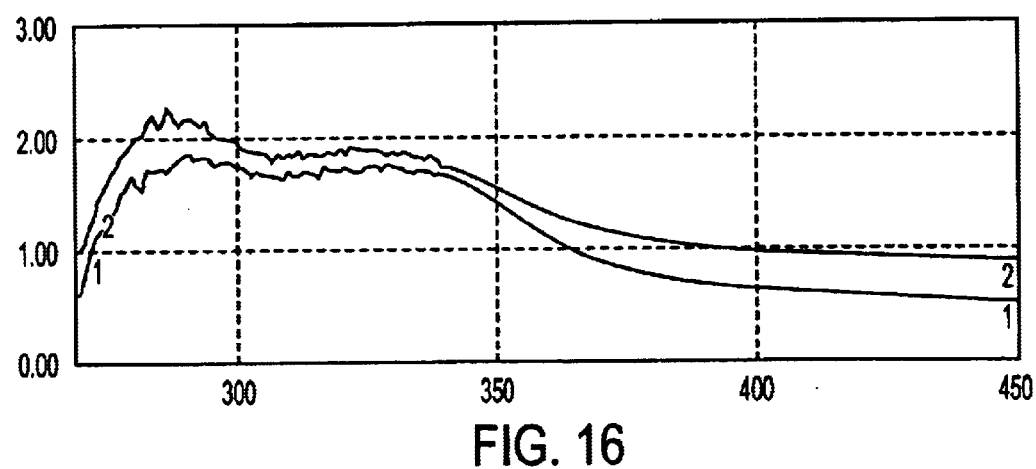

FIG. 16: Spectrophotometric scans of lipid films (Example 16) cetyl palmitate—Tego Care—Eusolex 4360, cetyl palmitate—Tego Care—Eusolex 4360—Aerosil 200

Figure 17:
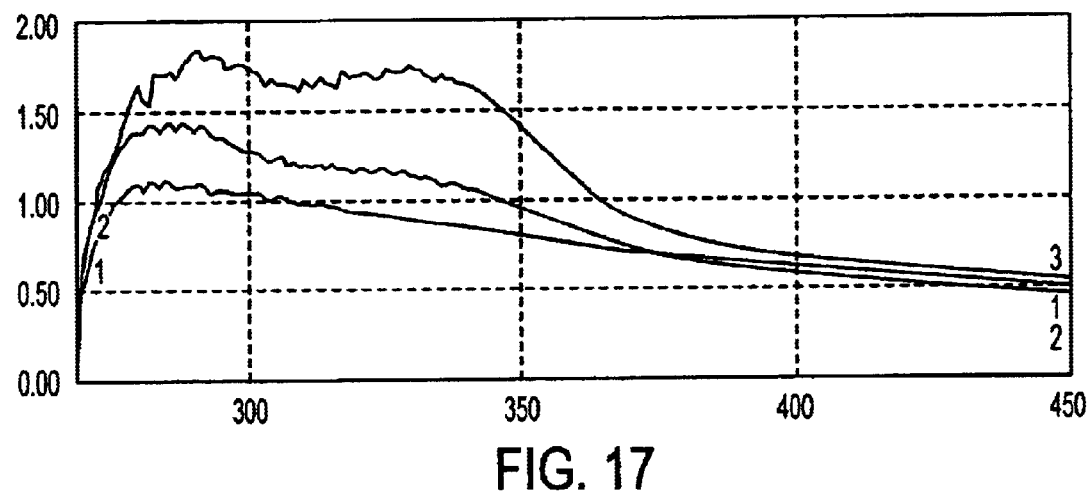

FIG. 17: Spectrophotometric scans of lipid films (Example 17) cetyl palmitate—Tego Care (self-absorption lipid particles), calculated absorption of cetyl palmitate Tego Care—Eusolex 4360—lipid particles, Absorption ascertained in practice of cetyl palmitate—Tego Care—Eusolex 4360—lipid particles (synergism)

Figure 18:

FIG. 18: Electron microscope photograph of the sealed lipid film from Example 18

DETAILED DESCRIPTION OF THE INVENTION

According to the invention, it was found that, for protection against UV radiation, a suspension of solid lipid particles can be used in which the suspension comprises lipid particles, dispersed in an outer phase (e.g. water), which have a solid matrix up to 20° C. The lipid particles are characterized in that in contrast to an oil-in-water emulsion, a melting peak is reached upon heating in differential scanning calorimetry (DSC) above 20° C. The lipid particles can be crystalline, but also partially crystalline (e.g. when there is a proportion of α-modification in the lipid).

The UV-blocking action of the agent was studied by measuring the UV absorption of the lipid particle dispersion in a UV spectrophotometer. The criterion was the reduced permeability of the lipid particle dispersion for UV radiation in the wavelength range up 280 nm (UV C), from 280 nm to 315 nm (=UV B) und from 315 nm to 400 nm (UV A). A further test to quantify the UV-blocking action was the determination of the reduced permeability of particle films using the standard test with Transpore™ tape (B. L. Diffey, P. M. Farr, Sunscreen protection against UVB, UVA and blue light; an in vivo and in vitro comparison, British Journal of Dermatology 124, 1991, 258–263). The particle films were produced by spreading the particle dispersion on Transpore™ tape and then air-drying. The films thus produced were then glued onto one side of a quartz cuvette and the UV permeability was determined by a photometer. The measurements took place against the corresponding references, e.g. O/W emulsion with the same lipid content as well as UV blockers incorporated into the oil phase of an emulsion.

The lipid particles are prepared by dispersion or precipitation of the lipid, using generally known methods described in pharmacy and process engineering textbooks. In the case of dispersion, coarsely dispersed lipids are dispersed and size reduced by mechanical processes. The lipids can be in a solid aggregate state (e.g. mortar mill) or liquid aggregate state (e.g. emulsification of molten lipids using mixers). To manufacture the lipid particle dispersion, the lipids can first be reduced in size and then dispersed in the outer (e.g. aqueous) phase or, alternatively, reduced in size directly in the outer phase. When reducing the size of lipid before dispersion in the outer phase, there can be used, for example: gas-jet mill, rotor-stator colloid mill and mortar mill.

The dispersion of the lipid in the outer phase can take place either in the solid state (cold dispersion) or in the liquid state (hot dispersion). With cold dispersion, the powdered lipid is dispersed in an aqueous surfactant solution (pre-dispersion) and then processed further with a suitable apparatus. With hot dispersion, the lipid is melted and poured into the outer phase. which has been heated to the same temperature, and dispersed therein (pre-emulsion). The obtained raw emulsion is then processed with a further dispersing apparatus. Depending on the required degree of dispersion, the concentration of the lipid phase, and the aggregate state of the lipid, there are used as dispersing systems, e.g. high-pressure homogenizers of the piston-gap homogenizer type (APV Gaulin systemne, French Press, Avestin), jet-stream homogenizers (e.g. microfluidizer), rotor-stator systems (Ultra-Turrax, Silverson-Homogenizers), ultrasound bath, ultrasound rod, ultrasound homogenizers, micro- und macroscale static mixers (e.g. Sulzer, Switzerland) as well as micromixers (=static micromixers from IMM GmbH, Mainz).

To produce the lipid particles by precipitation, the lipid is dissolved in a solvent and then mixed with a non-solvent. Due to the decrease in solubility, lipid particles precipitate. Alternatively, a microemulsion can also be produced with the molten lipid. The microemulsion obtained at increased temperature is then converted by breaking into a macroemulsion which forms solid lipid particles upon cooling. Breakage of the microemulsion can be achieved by simple cooling or the addition of water to the microemulsion. Alternatively, the microemulsion can also be poured into water, preferably cold water.

The particle size obtained when producing the lipid particle dispersion is a function of many parameters, e.g.:
Type of size reduction process
Surfactant concentration
Lipid concentration
Temperature Generally, in small-capacity processes such as when using a pestle, particles in the size range of ca. 50–100 $\mu$m are obtained. With a low surfactant concentration and high lipid concentration, high-speed mixers can produce particles with an average diameter in the range of a few $\mu$m to approx. 10–20 $\mu$m. With a high surfactant concentration and simultaneous low lipid concentration, particles in the nanometer range are also obtained. Superfine dispersions with particle sizes of up to approx. 50 nm are generally produced with high-pressure homogenization processes.

Many different lipids can be used to prepare lipid particle dispersions. These are both chemically uniform lipids and mixtures thereof. The lipids suitable according to the invention are characterized in that they are present in the dispersion in the crystalline state (e.g. $\beta$-, $\beta$i-modification) or liquid-crystalline state ($\alpha$-modification). A mixture of several such crystalline or liquid-crystalline lipids can also be present. In the lipid mixtures used, liquid lipids (e.g. oils, lipophilic hydrocarbons, lipophilic organic liquids such as oleyl alcohol) can also be added to the solid lipids (e.g. glycerides lipophilic hydrocarbons such as hard paraffin) (so-called "lipid blends").

The following lipids, for example, are employed as a dispersed phase and can be used as an individual component or as a mixture: natural or synthetic triglycerides or mixtures of the same, monoglycerides and diglycerides, alone or mixtures of the same or with e.g. triglycerides, self-emulsifying modified lipids, natural and synthetic waxes, fatty alcohols, including their esters und ethers as well as in the form of lipid peptides, or any mixtures of the same. Especially suitable are synthetic monoglycerides, diglycerides and triglycerides as individual substances or as a mixture (e.g. hard fat, Imwitor 900), triglyceride (e.g. glycerol trilaurate, glycerol myristate, glycerol palmitate, glycerol stearate and glycerol behenate) und waxes such as e.g. cetyl palmitate und white wax (DAB), additionally hydrocarbons, such as e.g. hard paraffin.

The following, for example, can be added as lipids liquid at room temperature (20° C.) to produce a lipid mixture (lipid blend): medium chain triglycerides (MCTs) such as Miglyol (e.g. Miglyol 812, Miglyol 810, Miglyol 840), long chain trigylcerides (LCTs) such as isopropyl myristate, vegetable oils such as avocado oil, cottonseed oil, safflower oil, peanut oil, jojoba oil, coconut oil, linseed oil, walnut oil, olive oil, palm-kernel oil, sesame oil, wheatgerm oil, animal oils such as cod-liver oil, halibut-liver oil, neat's foot oil, individually or in a mixture.

The proportion of the inner or lipid phase in the dispersion is 0.1% to 80% (weight/weight or m/m) and is preferably in the range of 1% to 40% (m/m) relative to the weight of the total dispersion. Should it be necessary or desired to add dispersion-stabilizing additives, e.g. emulsifiers, to be able to produce stable dispersions, these can be incorporated in the form of pure substances (e.g. individual surfactant) or in the form of mixtures (mixed emulsifiers, complex emulsifiers such as e.g. Lanette® N), in order to stabilize the particles. The amount of such additives in the dispersion is in the range of 0.01% to 30% and preferably in the range of 0.5% to 20%, relative to the total weight of the dispersion.

For the physical stabilization of the lipid particle dispersions or selective modification of the surface of the lipid particles, the surfactants, stabilizers and polymers can be used which are generally known from the manufacture of dispersions. Examples of these are:
1. sterically stabilizing substances such as poloxamers und poloxamines (polyoxyethylene-polyoxypropylene block copolymers), ethoxylated sorbitan fatty acid esters, in particular polysorbates (e.g. Polysorbat 80 or Tween 80®), ethoxylated mono- und diglycerides, ethoxylated lipids, ethoxylated fatty alcohols or fatty acids, and esters and ethers of sugars or of sugar alcohols with fatty acids or fatty alcohols (e.g. saccharose stearate, saccharose distearate, saccharose laurate, saccharose octanoate, saccharose palmitate, saccharose myristate).

2. charged ionic stabilizers such as diacetyl phosphates, phosphatidylglycerol, lecithins of various origins (e.g. egg lecithin or soya lecithin), chemically modified lecithins (e.g. hydrogenated lecithins), phospholipids and sphingolipids, mixture of lecithins with phospholipids, sterols (e.g. cholesterol and cholesterol derivatives such as stigmasterol) und saturated and unsaturated fatty acids, sodium cholate, sodium glycocholate, sodium taurocholate, sodium deoxycholate or their mixtures, amino acids or anti-flocculants such as e.g. sodium citrate, sodium pyrophosphate, sodium sorbate, amphoteric-ionic surfactants such as e.g. (3-[(3-cholamidopropyl)-dimethylammonio]-2-hydroxy-1-propane sulfonate) [CHAPSO], (3-[(3-cholamidopropyl)-dimethylammonio]-1-propane sulfonate) [CHAPS] and n-dodecyl-N,N-dimethyl-3-ammonio-1-propane sulfonate, cationic surfactants, in particular compounds used as preservatives, such as e.g. benzyldimethyl hexadecylammonium chloride, methylbenzethonium-chloride, benzalkonium chloride, cetylpyridinium chloride.

3. viscosity-increasing substances such as e.g. cellulose ethers and cellulose esters (e.g. methyl cellulose, hydroxyethyl cellulose, hydroxypropyl cellulose, sodium carboxymethylcellulose), polyvinyl derivatives such as polyvinyl alcohol, polyvinyl pyrrolidone, polyvinyl acetate, alginates, polyacrylates (e.g. Carbopol), xanthans und pectins.

If necessary or desired, the charged stabilizers are preferably included in the lipid particle dispersion in a quantity of 0.01% to 20% (m/m), relative to the total weight of the dispersion, and in particular of 0.05% to 10%.

If necessary or desired, viscosity-increasing substances are incorporated in a similar concentration in the formulation, preferably in a quantity of 0.01–20% and especially in a quantity of 0.1% to 10% (m/m) and preferably in the range between 0.5% and 5%, relative to the total weight of the dispersion.

There can be used as an outer phase (dispersion medium, continuous phase): water, aqueous solutions or liquids miscible with water, as well as glycerin or polyethylene glycols and oily liquids such as Miglyols (medium chain triglycerides—MCTs) and other oils (castor, peanut, soybean, cottonseed, rapeseed, linseed, olive, sunflower, safflower oils can be used. In principle, any liquid phase can be used as long as it does not dissolve or start to dissolve the lipid particles.

Surfactant-free lipid particle dispersions are manufactured by dispersing the lipid phase in an aqueous solution which includes one or more viscosity-increasing substances, either alone or in combination with other substances, as well as sugar, sugar alcohols, especially glucose, mannose, trehalose, mannitol, sorbitol and others. Furthermore, it is possible to use a combination of the viscosity-increasing substances or the combination of these with sugars or sugar alcohols, or in a further combination with charge stabilizers or anti-flocculants.

Particle formation for achieving a narrow particle size distribution and minimizing particle aggregates can be promoted by further additions. Such additions are substances which shift the pH value (e.g. increasing the zeta potential, influencing the surfactant structure as well as the degree of dissociation) or increase the stability of the lipid particle dispersion via other mechanisms, e.g. by influencing the water structure (e.g. addition of electrolytes) or by effects on the stabilizing surfactant layer (e.g. glucose in the case of lecithin).

The loading of the lipid particles with UV blocking substances, antioxidants such as tocopherol and skin-care substances (e.g. retinol and its derivatives, urea)—grouped here as "active ingredients"—can take place in different ways, individually or in combination. The active ingredient (s) are dissolved in the lipid particles, solubilized (e.g. with surfactants or cyclodextrins) or dispersed. Furthermore, they can be absorbed at their surface. Due to the solid character of the particle matrix, hydrophilic active ingredients in the form of an aqueous active ingredient solution can also be incorporated in the lipid phase. After this incorporation and the following dispersion of the lipid in the aqueous dispersion medium, a W/F/W system results, i.e. water in fat in water. Due to its solid aggregate state, the lipid nucleus incorporates the aqueous active ingredient solution better than is possible with comparable multiple water-in-oil-in-water emulsions (W/O/W).

The incorporation of active ingredients can take place according to different methods. The following may be cited by way of example:
1. Dissolving the active ingredient in the inner (e.g. molten) phase.
2. Dissolving the active ingredient in a solvent miscible with the inner phase and adding this active ingredient solution to the inner phase. The solvent is optionally then partially or completely removed.
3. Dispersing the active ingredient in the inner phase (e.g. by dispersing a solid such as titanium dioxide or selective precipitation in the inner phase).
4. Dissolving the active ingredient in the outer, aqueous phase (e.g. amphiphilic substances) and incorporating the active ingredient into a surfactant film which stabilizes the lipid particles during manufacture.
5. Absorption of the active ingredient at the particle surface.
6. Dissolving the active ingredient in the lipid phase by means of a solubilizer (e.g. of a block copolymer, sorbitan fatty acid ester, cyclodextrin), then dispersing the lipid phase to produce the pre-dispersion. The active ingredient is then present as a solid solution in the particles.
7. Incorporating aqueous active ingredient solutions into the lipid phase and then dispersing the lipid phase to produce the pre-dispersion so that a W/F/W system forms which is analogous to the multiple emulsions.
8. Dispersing the active ingredient in the molten lipid phase via a swelling or gel-forming process (e.g. Aerosil as oleogel former in molten lipid).

According to the invention, the following, among others, can be used as molecular UV blockers: benzophenone and its derivatives such 4-phenyl-benzophenone, 2-hydroxy-4-n-octyloxybenzophenone, 2-hydroxy-4-methoxybenzophenone, 2,2'-dihydroxy-4,4'-dimethoxybenzophenone, sulisobenzone, benzimidazole derivatives such as phenylbenzimidazole sulfonic acid, camphor derivatives such as 3-benzylidene camphor, 3-(4-methyl-benzyliden)camphor, terephthalylidenedicamphor sulfonic acid, dibenzoylmethanes such as 4-isopropyl-dibenzoylmethane, 4-tert-butyl-4'-methoxy-dibenzoylmethane, cinnamic acid esters such as p-methoxycinnamic acid-2-ethylhexyl ester, p-methoxy-cinnamic acid isoamyl ester, p-methoxycinnamic acid octyl ester, p-methoxycinnamic acid propyl ester, p-aminobenzoic acid (PABA) and its derivatives such as p-aminobenzoic acid glycerolester, butyl-PABA, octyl-dimethyl-PABA, or other substances such as 2-ethylhexyl salicylate, homosalate, Mexoryl® SX, Mexoryl® XL, octylsalicylate, octyltriazone, oxybenzone, individually or in a mixture.

According to the invention, the following, among others, can be used as inorganic pigments or organic pigments (particulate UV blockers): barium sulphate, bentonite, calcium carbonate, calcium sulphate, ferric (III) oxides, ferric hydroxide, kaolin, carbon black, copper oxide, magnesium oxide, silver, silicon dioxide (e.g. Aerosils), Syloid, hydrophobic alkylated silicon dioxide (e.g. Aerosil R972), talcum, titanium dioxide, bismuth oxychloride, zinc oxide, zinc stearate, melanin, individually or in a mixture.

According to the invention, the following, among others, can be used as antioxidative substances: retinol, retinol derivatives such as retinol palmitate, retinol acetate, vitamin E, vitamin E derivatives such as vitamin E acetate, vitamin E linoleate, vitamin E nicotinate, vitamin E palmitate, vitamin E-POE(22) succi-nate, vitamin C, vitamin C derivatives such as e.g. vitamin C-palmitate, magnesium ascorbate, magnesium phosphate, aescine, butylhydroxyanisole (BHA), butylhydroxytoluene (BHT), cysteine, dilaurylthiodipropionate, dodecylgallate, caffeic acid propylgallate, individually or in a mixture.

According to the invention, the following, among others, can be used as skin-care substances and/or moisturizing substances: amino acid derivatives such as arginine pyroglutaminate, glutamic acid, lysine pyroglutaminate, glucose, glycerol, urea, mucopolysaccharides such as hyaluronic acid, sodium lactate, sodium pyrrolidone carboxylic acid, propylene glycol, retinols, vitamin A and its derivatives, saccharose glutamate, allantoin, biotin, bisabolol, cholesterol, collagen and its derivatives, elastin, glycoproteins, hyaluronic acid and its derivatives, keratin and its derivatives, lecithin, linoleic acid, linolenic acid, milk proteins, niacinamide, panthenol and its derivatives, riboflavin, sulphur, urea, soybean oil, tocopherol and its derivatives, individually or in a mixture.

To manufacture and characterize the lipid particles in the examples, the following apparatus was used: Ultra-Turrax T25, Janke and Kunkel, Staufen, with dispersing tool S25 KR; Micron Lab 40, APV Homogenizer, Lübeck; Coulter LS230, Coulter Electronics, Krefeld; Zetasizer 4, Malvern Instruments, Essen; Uvikon 940 Spectrophotometer, Kontron, Neufahn; Scanning Electron Microscope S360, Cambridge Instruments (England).

The lipids, surfactants and UV blockers used were: Precifac ATO, Gattefossé (Frankreich); Tego Care 450, Th. Goldschmidt, Essen; stearyl alcohol, Fluka, Neu-Ulm; Tween 80, Merck, Darmstadt; Eusolex 4360, Merck, Darmstadt.

The particles strengthen the natural skin barrier by forming a sealed lipid film when spread on (Example 18). In contrast to the known perforated porous film formation with a dense spherical packing, upon spreading of the lipid particle dispersion to produce films, the formation of a sealed lipid film was observed and demonstrated by an electron microscopy. A damaged natural lipid barrier of the skin can thereby be repaired or replaced.

To manufacture sunscreens, lipid particle dispersions with a higher lipid content (e.g. >approx. 40%) relative to the total weight of the dispersion can be produced (i.e. for example, >40 g lipid in 100 g dispersion), which, due to the high solids concentration, generally have a sufficiently high consistency so that they are suitable for application to the skin. In lipid particle dispersions having a lower concentration, it may be necessary to increase the viscosity of the outer phase, e.g. by adding a gelation agent. The choice of gelation agent depends on the chemical nature of the outer phase (e.g. hydroxyethyl cellulose in the case of water, Aerosil in the case of water or oil, etc.). Alternatively, the lipid particles according to the invention can be added to lotions (e.g. O/W emulsions), creams or ointments or incorporated into these. Coarsely dispersed lipid particles can therefore be added by stirring the lipid powder into these systems. Superfine lipid particles (e.g. in the nanometer range) can be added as a dispersion with a higher concentration. Alternatively, lipid particle dispersions can be incorporated direct during the manufacture of lotions and creams, by replacing a part of the water phase with a lipid particle dispersion having a sufficiently high concentration.

EXAMPLES

Example 1

UV-blocking Action of Cetyl Palmitate Particles Compared with Miglyol Emulsions

A lipid particle dispersion consisting of 10% (m/m) cetyl palmitate, 1.2% (m/m) polyglycerol methylglucose distearate (Tego Care 450) and water was produced by high pressure homogenization. The mixture of lipid and emulsifier was melted at 75° C. and dispersed in the aqueous solution with an Ultra-Turrax T25 with dispersing tool S25, Janke und Kunkel (8000 rpm for 1 minute). The obtained pre-emulsion was then homogenized with an APV Gaulin LAB 40 homogenizer at 500 bar with 3 cycles at 75° C. Lipid particles resulted with a PCS diameter of 221 nm and a polydispersity index of 0.06. For comparison, an emulsion system was produced in which the 10% cetyl palmitate was replaced by 10% Miglyol 812. The production parameter was dispersion with the Ultra-Turrax (8000 rpm for 1 minute). The UV-blocking action was examined with a Uvikon 940 spectrophotometer, Kontron, in the wavelength range of 250–450 nm. For this, the lipid particle dispersion and emulsion were diluted (5 µL in 1 ml water), and measurement was against water. Over the measured range, the emulsion showed a constant absorption of approx. 0.15 and the lipid particle dispersion an absorption increase of from 0.1 at 450 nm to 0.45 at 250 nm. Measurements of a pure lipid solution (in 96% ethanol) or an aqueous surfactant solution of the same concentration did not absorb over the whole measurement range (FIG. 1).

Example 2

UV-blocking Action of Stearyl Alcohol Lipid Particles

Figure 2:
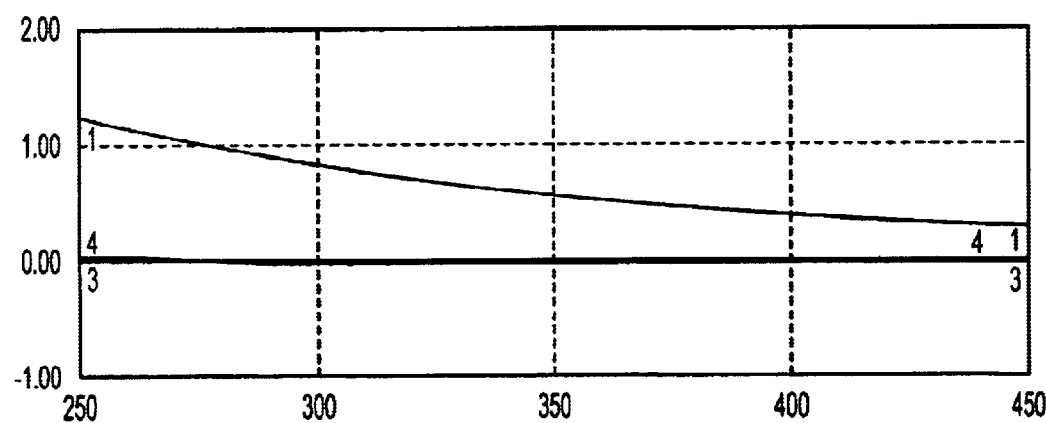

Lipid particles und emulsions were produced as in Example 1; the surfactant was 1.2% Polysorbat 80 (Tween 80). In the spectrophotometer, the Miglyol emulsion merely showed an absorption value of 0–0.05 over the whole range (i.e. this is near to the background noise of the apparatus); the stearyl alcohol lipid particles had an absorption increasing from 0.3 at 450 nm to 1.3 at 250 nm. Measurements of a pure lipid solution (in 96% ethanol) or an aqueous surfactant solution of the same concentration did not absorb over the whole measurement range (FIG. 2).

Example 3

UV-blocking Action of Lipid Particles After Formation of a Film

A lipid particle dispersion was prepared according to Example 1 with cetyl palmitate and the surfactant polyglycerol methylglucose distearate (Tego Care 450). For comparison, the emulsion with Miglyol and the surfactant Tego Care was produced as described in Example 1. The two formulations were applied to a Transpore™ tape stuck onto a quartz measuring cuvette (50 μl on 4.5 cm² Transpore™ tape) and immediately measured. The UV-blocking action of the films which formed was examined in the spectrophotometer, uncoated Transpore™ tape being stuck onto a cuvette as reference. Over the measured range (450–250 nm), the result for the emulsion film was a relatively constant absorption of 0.25–0.30; the absorption of the lipid particles increased from 0.45 at 450 nm to 1.1 at 280 nm (FIG. 3).

Example 4

Increase in Absorption in Relation to the Lipid Concentration

Figure 4:
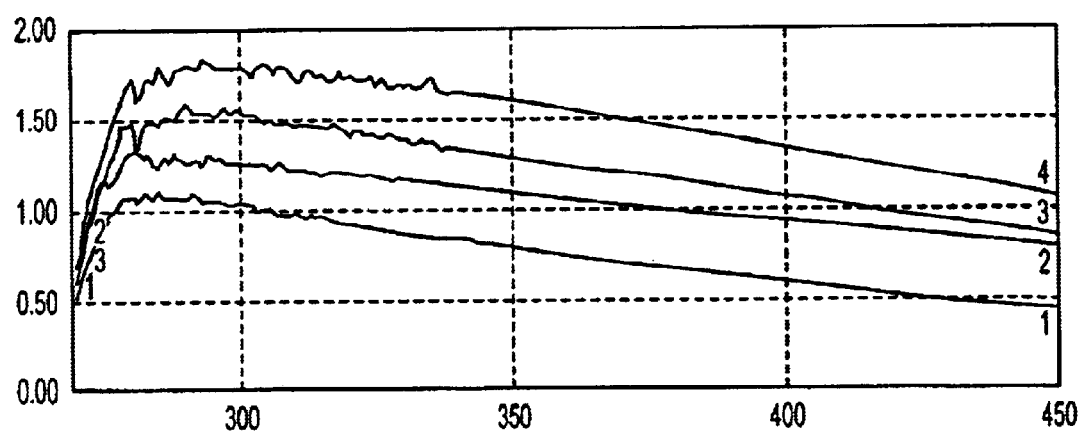

Lipid particles comprising cetyl palmitate stabilized with Tego Care were produced at different lipid concentrations. The lipid concentrations were 10%, 20%, 30% und 40% with proportional Tego Care concentrations of 1.2%, 2.4%, 3.6% and 4.8%. The corresponding laser diffractometry LD 50% diameters were 138 nm, 214 nm, 142 nm and 178 nm, with an increasing lipid concentration. The absorption of the films applied to Transpore™ w tape analogously to Example 3 increased in relation to the concentration (FIG. 4).

| lipid concentration | absorption at 450 nm | absorption at 280 nm |
| --- | --- | --- |
| 10% | 0.45 | 1.1 |
| 20% | 0.8 | 1.33 |
| 30% | 0.9 | 1.58 |
| 40% | 1.1 | 1.8 |

Example 5

UV-blocking Action as a Function of Particle Size

Figure 5:
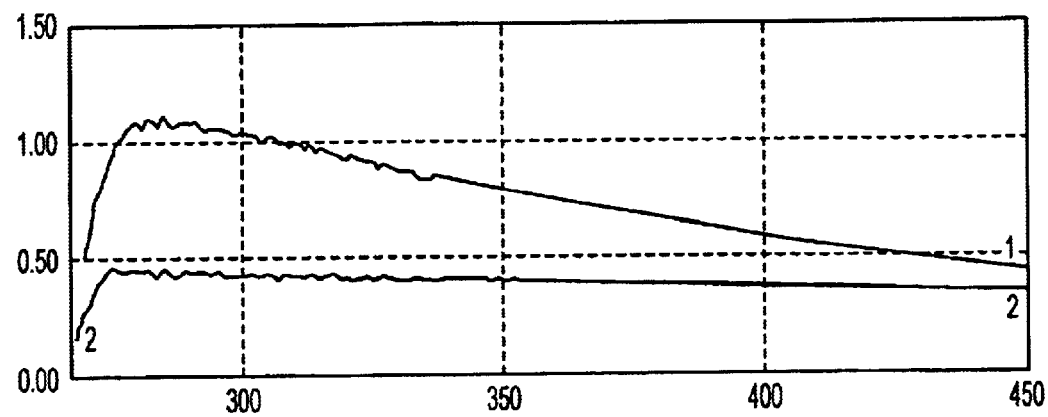

Lipid particles were produced analogously to Example 1. The composition was 10% lipid, 1.2% surfactant and water. Manufacture of the lipids took place by dispersion in the molten state (75° C.) with a high-speed Ultra-Turrax mixer (8000 rpm for 5 minutes) and alternatively by high-pressure homogenization (conditions as in Example 1). The particle size with the mixer was 4.6 μm (d50%–50% diameter), the particle size after high-pressure homogenization 138 nm (d50%). Both lipid particle dispersions were applied to Transpore™ tape as described in Example 3 and after drying at room temperature were immediately measured in the UV spectrophotometer. The absorption over the whole measurement range was roughly 0.45 for the lipid micro-particles and increased for the lipid nanoparticles produced by high-pressure homogenization, from 0.45 at 450 nm to 1.1 at 280 nm (FIG. 5).

Example 6

Stability of the Solid Lipid Particles After Incorporation Into a Cream

Lipid particles with the following composition were produced: 10% cetyl palmitate, 1.2% polyglycerol methylglucose distearate (Tego Care 450) and water. The mixture of lipid and emulsifier was melted at 75° C. and dispersed in the aqueous solution with an Ultra-Turrax T25 with dispersing tool S25, Janke and Kunkel (8000 rpm, for 1 minute). The pre-emulsion obtained was then homogenized with an APV Gaulin LAB 40 homogenizer at 500 bar with 3 cycles at 75° C. Lipid particles formed with a PCS diameter of 220 nm and a polydispersity index of 0.06. The lipid particles were mixed in the ratio of 1:1 with an O/W-emulsion obtainable in the trade. The mixing took place by stirring in a fanta bowl with a pestle. The integrity of the particles was determined by differential scanning calorimetry (DSC). The melting peak of the lipid particle dispersion was 16.8 J/g; after incorporation of an equivalent amount of lipid particle dispersion into the cream, the melting peak in the cream was 16.6 J/g. The particles were physically stable for 6 months. After 6 months storage at 20° C., the melting peak was 16.2 J/g and was not significantly different from the initial value (FIG. 6).

Example 7

UV-blocking Action of Polymer Particles as a Function of the Particle Size 2.5 latex dispersions with particle sizes of 60 nm, 100 nm, 528 nm, 949 nm und 3000 nm were applied to Transpore™ Tape analogously to Example 3 and immediately measured over the range from 450 nm to 250 nm. For particle sizes up to 528 nm, the following applies: the larger the particle, the greater the absorption. Above approx. 1 μm, the absorption decreases again (more pronounced decrease in the longer-wave range) (FIG. 7).

Example 8

Uniformity of the Films Applied to Transpore™ Tape

Figure 8:
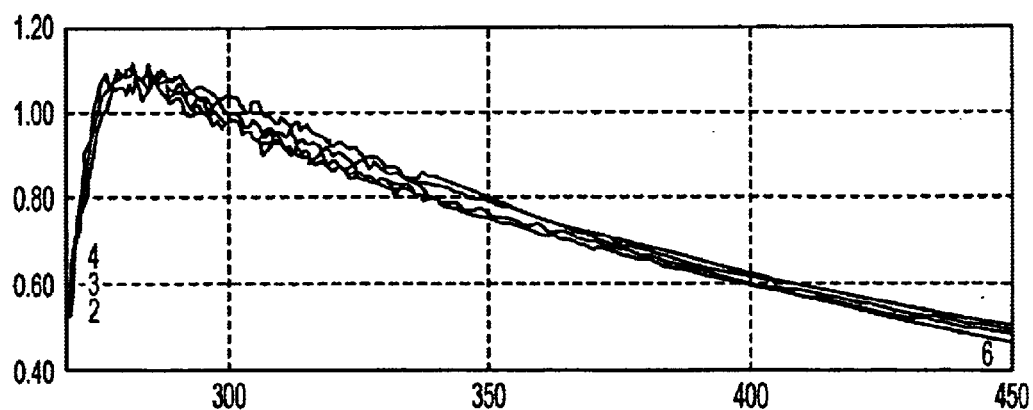

A lipid particle dispersion of 10% cetyl palmitate, 1.2% polyglycerol methylglucose distearate (Tego Care 450) and water was produced. 50 μl of this dispersion was uniformly applied to a 4.5 cm² area of a quartz cuvette stuck on with Transpore™ tape and measured over the wavelength range from 450% 250 nm. The cuvette was secured in the holder in different positions and the film thus measured over a length of 8 mm. The absorption values hardly fluctuate, and so the film was uniform (FIG. 8).

Example 9

Figure 9:
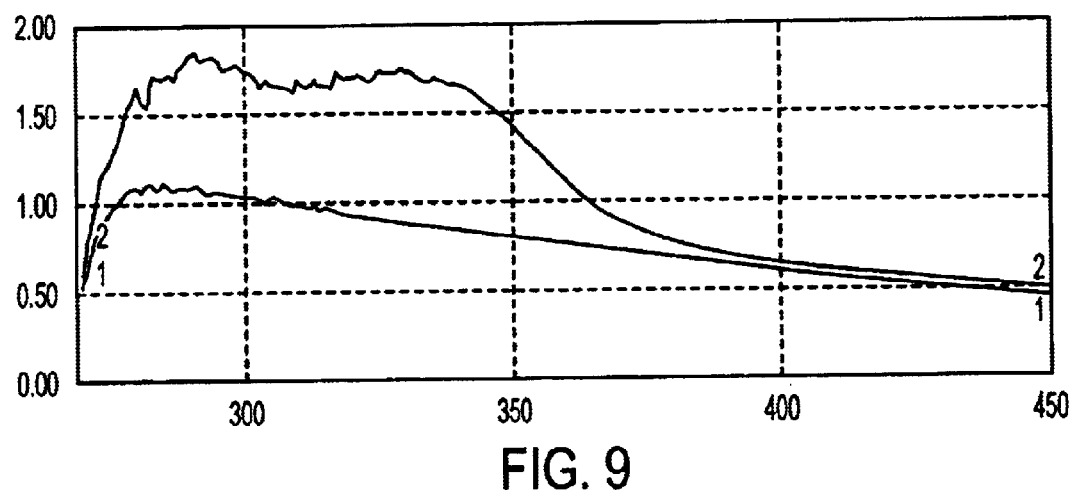

UV-blocking Action of UV Blocker-containing Lipid Articles After Formation of a Film A lipid particle dispersion was produced according to Example 1 with cetyl palmitate and the surfactant polyglycerol methylglucose distearate (Tego Care 450), the lipophilic broadband filter 2-hydroxy-4-methoxy-benzophenone (Eusolex 4360) being melted with the lipid phase in a concentration of lot relative to the lipid (corresponds to 1% relative to the total mixture) and thus incorporated. The pure lipid particle dispersion, prepared as described in Example 1, served as a comparison. The two formulations were applied to a Transpore™ tape (50 μl on 4.5 cm² Transpore™ tape) stuck onto a quartz measurement cuvette, spread and immediately measured. The UV-blocking action of the formed films was examined in the spectrophotometer, uncoated Transpore™ tape being stuck onto a cuvette as reference. In the range below 380 nm, the dispersion containing UV blocker showed a clearly higher absorption, with the pattern typical of Eusolex 4360 (peaks at approx. 335 und 290 nm), than the pure lipid particles (FIG. 9).

Example 10

Increase in Absorption in Relation to the UV Blocker Concentration

Figure 10:
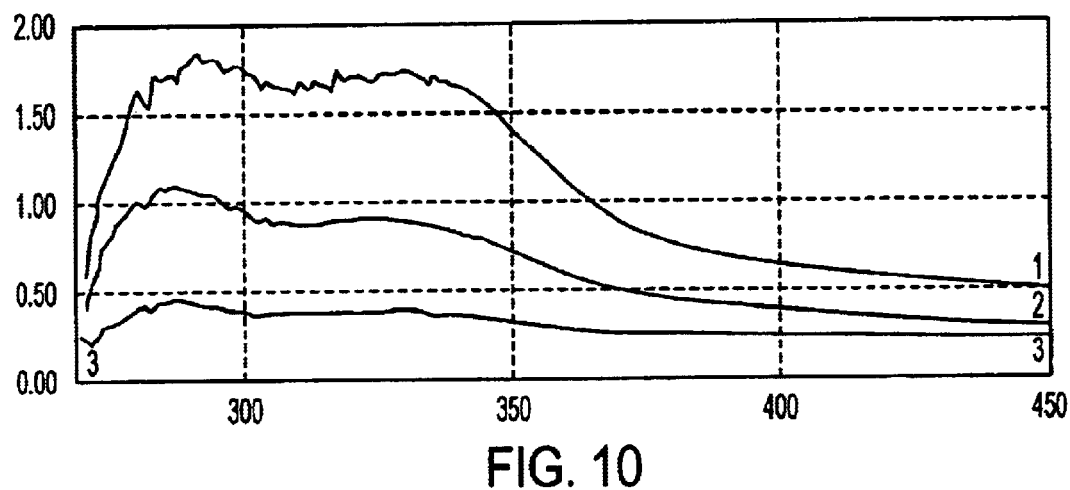

Lipid particle dispersions were produced according to Example 1 with 10% cetyl palmitate, 1.2% polyglycerol methylglucose distearate (Tego Care 450) and water whereby 10%, 5%, and 1% 2-hydroxy-4-methoxy-benzophenone (Eusolex 4360) being incorporated relative to the lipid analogously to Example 9. The dispersions were applied to Transpore™ Tape and measured, according to Example 3. The absorption was concentration-related, though not proportionally (FIG. 10).

Example 11

UV-blocking Action of UV Blocker-containing Lipid Particles After Formation of a Film A lipid particle dispersion was produced according to Example 9 with cetyl palmitate, the surfactant polyglycerol methylglucose distearate (Tego Care 450) and 10% 2-hydroxy-4-methoxy-benzophenone (Eusolex 4360), relative to the lipid content. The emulsion with Miglyol and the surfactant TegoCare, produced as described in Example 1 served as reference, 10% Eusolex, relative to the Miglyol content, also being incorporated here. The two formulations were applied to a Transpore™ tape stuck to a quartz measuring cuvette, (50 µl on 4.5 cm² Transpore™ tape), spread and immediately measured. The UV-blocking action of the formed films was examined in the spectrophotometer, uncoated Transpore™ tape being stuck to a cuvette as reference. Over the measured range (450–250 nm), the result for the emulsion film was an absorption which was clearly below the absorption of the lipid particle dispersion (FIG. 11).

Example 12

UV-blocking Action After Incorporation of a UV Blocker as a Function of Particle Size Lipid particles were produced analogously to Example 9. The composition was 10% lipid, 1.2% surfactant, 10% UV blocker relative to the lipid content, and water. Production of the lipids took place by dispersion in the molten state (75° C.) with a high-speed Ultra-Turrax mixer (8000 revolutions per minute, 5 minutes) und alternatively with high pressure homogenization (conditions as in Example 1). The particle size with the mixer was 12 µm (d50%), the particle size after high pressure homogenization 138 mm (d50%). Both lipid particle dispersions were applied to Transpore™ tape as described in Example 3 and, after drying at room temperature, immediately measured in the UV spectrophotometer. In the whole UV range, the absorption of the microparticles was clearly below the absorption of the nanoparticles (FIG. 12).

Example 13

UV-blocking Action After Incorporation of a UV Blocker and a Skin-care Drug Lipid particles of 10% cetyl palmitate, 1,2% polyglycerol methylglucose distearate (Tego Care 450) und 10% 2-hydroxy-4-methoxy-benzophenone (Eusolex 4360) (the latter relative to the lipid content) were produced according to Example 9, retinol palmitate being incorporated as a further constituent in a concentration of 0.2% relative to the total mixture by joint melting-on with the lipid phase. The lipid particle dispersion was measured as film, analogously to Example 3, the lipid particle dispersion containing only UV blocker serving as reference. Over the whole measurement range, the lipid particles containing vitamin A palmitate showed only minor deviations from the reference (FIG. 13).

Example 14

UV-blocking Action of Lipid Particles After Incorporation of a UV Blocker and an Antioxidant Lipid particles of 10 cetyl palmitate, 1.2% polyglycerol methylglucose distearate (Tego Care 450) and 10% 2-hydroxy-4-methoxy-benzophenone (Eusolex 4360) (the latter relative to the lipid content) were produced according to Example 9, tocopherol being incorporated as a further constituent in a concentration of 2% relative to the total mixture by joint melting-on with the lipid phase. The lipid particle dispersion was measured as film, analogously to Example 3, the lipid particle dispersion containing only UV blocker serving as reference. Over the whole measuring range, the lipid particles containing vitamin E showed only minor deviations from the reference (FIG. 14).

Example 15

UV-blocking Action of Aerosil-containing Lipid Particles After Formation of a Film A lipid particle dispersion was produced with cetyl palmitate and the surfactant polyglycerol methylglucose distearate (Tego Care 450) according to Example 1, highly-dispersed silicon dioxide (Aerosil 200) being melted on in a concentration of 5% relative to the lipid content jointly with the lipid phase, allowed to swell for 5 minutes at 75° C. and thus incorporated. The pure lipid particle dispersion produced as described in Example 1 served as a comparison. The two formulations were applied to a Transpore™ tape stuck to a quartz measurement cuvette (50 µl on 4.5 cm² Transpore™ tape) spread and immediately measured. The UV-blocking action of the formed films was examined in the spectrophotometer uncoated Transpore™ tape, being stuck onto a cuvette as a reference. The lipid particle dispersion, which additionally contained Aerosil, was recognizably more absorbent than the comparison formulation (FIG. 15).

Example 16

UV-blocking Action of Aerosil-containing and UV Blocker-containing Lipid Particles After Formation of a Film A lipid particle dispersion was produced with the UV blocker 2-hydroxy-4-methoxy-benzophenone (Eusolex 4360) (10% relative to the lipid), analogously to Example 9, 5% Aerosil 200, relative to the lipid, additionally being incorporated as in Example 15. The same formulation, but without Aerosil 200, served as a comparison. The two formulations were applied to a Transpore™ tape stuck to a quartz measuring cuvette (50 µl on 4.5 cm² Transpore™ tape) spread and immediately measured. The UV-blocking action of the formed films was examined in the spectrophotometer uncoated Transpore™ tape being stuck onto a cuvette as a reference. The lipid particle dispersion, which additionally contained Aerosil, was more absorbent than the comparison formulation (FIG. 16).

Example 17

Synergism of Solid Lipid Nanoparticles and UV Blockers as Films

The self-absorption of the UV blocker 2-hydroxy 4-methoxy-benzophenone (Eusolex 4360) was computed by subtracting the absorption of the Miglyol—Tego Care emulsion (s. Example 3) from the absorption of the Eusolex 4360-containing Miglybl—Tego Care emulsion (s. Example 11) over the 450to 250 nm range. These values were added to the absorption of pure lipid particles (s. Example 3) to obtain the theoretical absorption of lipid particles containing UV blockers. However, if the theoretical absorption of lipid particles which contain Eusolex 4360 is compared with that measured in practice, a synergism is recorded, as the theoretical absorption is lower over the whole UV range (FIG. 17).

Example 18

A lipid particle dispersion consisting of 10% cetyl palmitate 1.2% Tego Care 450 and water, produced analogously to Example 1, was applied to double-sided adhesive Sellotape, allowed to dry overnight and examined with an S 360 scanning electron microscope from Cambridge Instruments. A sealed lipid film was detected (FIG. 18).

What is claimed is:

1. UV-protection composition comprising:
    solid, polymorphic lipid particles that are crystalline or partially crystalline, optionally in the form of a solid inner phase (lipid phase) dispersed in an outer liquid phase, wherein the solid polymorphic particles have an endothermic peak above 20° C. during the heating-up phase in heat calorimetry (DSC—differential scanning calorimetry) and have a size (average value of the main population) in the range of 10 nm to 1000 nm, and wherein the polymorphic particles comprise at least one selected from the group consisting of natural and synthetic mono-, di- und triglycerides, their mixtures, fatty alcohols, ethers of the same, individually or in a mixture, cetyl palmitate, glycerol monostearate, glycerol palmitostearate, glycerol ricinoleate, glycerol tribehenate (Compritol), gly-cerol trilaurate, hard fat (Witepsols), microcrystalline triglycerides (Dynasanes), and stearyl alcohol, individually or in a mixture.

2. Composition according to claim 1, further comprising one or more molecular and/or particulate UV blockers which are dissolved and/or dispersed in lipid the matrix material and/or adsorbed at the surface of the lipid particles.

3. Composition according to claim 2, comprising as particulate UV blocker one or more inorganic pigments or organic pigments which is/are dispersed in the lipid matrix and/or is/are added to the surface of the lipid particles.

4. Composition according to claim 3, wherein the pigment comprises at least one selected from the group consisting of barium sulphate, bentonite, calcium carbonate, calcium sulphate, ferric(III) oxides, ferric hydroxide, kaolin, carbon black, copper oxide, magnesium oxide, silver, silicon dioxide, Aerosil, Syloid, hydrophobic alkylated silicon dioxide, Aerosil R972, talcum, titanium dioxide, bismuth oxychloride, zinc oxide, zinc stearate and melanin, individually or in a mixture.

5. Composition according to claim 1, further comprising one or more antioxidative substances, individually or in a mixture, which are dissolved and/or dispersed and/or absorbed in the lipid matrix and/or adsorbed at the surface of the lipid particles.

6. Composition according to claim 5, wherein the antioxidative substance comprises at least one selected from the group consisting of retinol, retinol derivatives, retinol palmitate, retinol acetate, vitamin E, vitamin E derivatives, vitamin E acetate, vitamin E linoleate, vitamin E nicotinate, vitamin E palmitate, vitamin E-POE (22) succinate, vitamin C, vitamin C derivatives, vitamin C palmitate, magnesium ascorbate, magnesium phosphate, aescine, butylhydroxyanisole (BHA), butylhydroxytoluene (BHT), cysteine, dilaurylthiodipropionate, dodecylgallate, caffeic acid, liponic acid and derivatives, propylgallate, flavonoid, rutin, a derivative of rutin, quercetin, a derivative of quercetin, and tanning agents, individually or in a mixture.

7. Composition according to claim 1, further comprising at least one skin-care substance and/or moisturizing substance which is dissolved and/or dispersed in the lipid matrix and/or are adsorbed at the surface of the lipid particles.

8. Composition according to claim 7, wherein the skin-care substance and/or moisturizing substance comprises at least one selected from the group consisting of, amino acid derivatives, arginine pyroglutaminate, glutamic acid, lysine pyroglutaminate, glucose, glycerol, urea, mucopolysaccharide, hyaluronic acid, sodium lactate, sodium pyrrolidone carboxylic acid, propylene glycol, vitamin A, retinols, a derivative of retinol, polysaccharides, uronic acids, saccharose glutamate, allantoin, biotin, bisabolol, cholesterol, collagen, a derivative of collagen, elastin, glycoproteins, hyaluronic acid, a derivative of hyaluronic acid, keratin, a derivative of keratin, lecithin, linoleic acid, linolenic acid, milk proteins, niacinamide, panthenol, a derivative of panthenol, riboflavin, sulphur, urea, soybean oil, tocopherol, and a derivative of tocopherol, individually or in a mixture.

9. Composition according to claim 1, further comprising at least one natural, synthetic, or semi-synthetic scents, individually or in a mixture, which are dissolved and/or dispersed in the lipid matrix and/or adsorbed at the surface of the lipid particles.

10. Composition according to claim 9, wherein the natural, synthetic or semi-synthetic scent comprises at least one selected from the group consisting of ethereal oils, perfumes, pheromones and repellents.

11. Composition according to claim 10, comprising at least one ethereal oil selected from the group consisting of lemon oil, rose oil, lavender oil, bergamot oil, balm mint oil, clove oil, cinnamon oil, orange oil, jasmine oil, rosemary oil, aniseed oil, peppermint oil, sandalwood oil, ylang-ylang oil, ylang-ylang oil isolated ingredients, 1,8-cineole, menthol, terpinol hydrate, limonene, α-pinene and eugenol.

12. Composition according to claim 10, comprising at least one perfume selected from the group consisting of Allure, Coco, Egoiste, Chanel No. 5, 19, 22 from Chanel, Miss Dior, Dune, Diorissime or Fahrenheit from Dior, Roma, Laura, Venezia from Laura Biagotti, L'air du temps from Nina Ricci, Chalimar from Guerlain, Tresor from Lancome, Gio from Armani, Escape, Obsession, CK One, CK be, Eternity from Calvin Klein, Berlin, Joop, Rococo, All about Eve, What about Adam, Nightflight from Joop, KL, Lagerfeld, Jako from Karl Lagerfeld and Extreme from Bulgari.

13. Composition according to claim 10, comprising at least one repellent selected from the group consisting of natural repellents, citrus oils, eucalyptus oil, camphor, synthetic repellents, N,N-diethyl-toluamide (DEET), dibutyl phthalate, dimethyl phthalate and 2-ethyl-1,3-hexandiol.

14. Composition according to claim 1, wherein the lipid particles comprise lipids/lipoids that are solid at room temperature (20° C.).

15. Composition according to claim 1, wherein the lipid particles comprise at least one lipid solid at room temperature (20° C.), to which at least one lipid liquid at room temperature is added to produce a lipid mixture.

16. Composition according to claim 15, wherein the liquid lipid comprises at least one selected from the group consisting of medium chain triglycerides (MCTs), Miglyol, Miglyol 812, Miglyol 810, Miglyol 840, long chain triglycerides (LCTs), isopropyl myristate, vegetable oils, avocado oil, cotton-seed oil, safflower oil, peanut oil, jojoba oil, coconut oil, linseed oil, walnut oil, olive oil, palm-kernel oil, sesame oil, wheatgerm oil, animal oils, cod-liver oil, halibut-liver oil, and neat's foot oil, individually or in a mixture.

17. Composition according to claim 1, wherein the lipid particles were produced by grinding.

18. Composition according to claim 1, wherein the lipid particles were produced by dispersing the lipid in an outer liquid phase, the lipid being in the solid and/or liquid state.

19. Composition according to claim 18 wherein the lipid has been dispersed in an outer phase below its melting point.

20. Composition according to claim 18, wherein the lipid has been dispersed in an outer phase close to or above its melting point.

21. Composition according to claim 1, wherein the lipid particles are dispersed in the outer liquid phase and are stabilized by surfactants, polymers or antiflocculants and/or a stabilization against particle aggregation has been effected by increasing the viscosity of the liquid phase by adding viscosity-increasing substances.

22. Composition according to claim 21, comprising at least one surfactant selected from the group consisting of sorbitan fatty acid esters, Tween, Tween 80, Span, Span 85, sugar esters, saccharose stearate, saccharose distearate, saccharose laurate, saccharose octanoate, saccha-rose palmitate, saccharose myristate, fatty alcohols, cetylstearyl alcohol, sodium cetylstearyl sulphate, cocoamidopropylbetain (Tego Betain L7FG), sodium cocoamphoacetate (Miranol Ultra 32), polyglycerol methylglucose distearate (Tego Care 450), lecithins, soybean lecithin or egg lecithin, alkaline soaps, metal soaps, calcium dilaurate, natural surfactants, and saponins, individually or in a mixture.

23. Composition according to claim 21, comprising at least one polymer selected from the group consisting of block polymers, poloxamers, Poloxamer 188, Poloxamer 407, polyvinyl derivatives, polyvinyl acetate, polyvinyl alcohol, polyvinyl pyrrolidone, and polystyrenes, individually or in a mixture.

24. Composition according to claim 21, comprising at least one antiflocculant selected from the group consisting of sodium citrate, sodium pyrophosphate and sodium sorbate individually or in a mixture.

25. Composition according to claim 21, comprising at least one viscosity-increasing substance selected from the group consisting of cellulose derivatives, carboxymethyl cellulose, cellulose acetate phthalate, hydroxyethyl cellulose, methyl cellulose, methylhydroxyethyl cellulose, methylhydroxypropyl cellulose, polyacrylates, polyacrylic acids, polyvinyl derivatives, alginates, bentonite, highly-dispersed silicon dioxide (Aerosil), pectins, tragacanth and xanthan, individually or in a mixture.

26. Composition according to claim 1, wherein the outer phase of the dispersion further comprises at least one additional UV blocking substance and/or UV blocking particle.

27. Composition according to claim 1, wherein it is present in the form of a formulation for application on skin and mucous membranes.

28. Composition according to claim 1, wherein it is present in the form of a formulation for application on hair or scalp.

29. Method for protecting skin, mucous membranes, hair or scalp against health-damaging UV radiation and strengthening the natural skin barrier comprising applying a UV radiation-absorbing and/or reflecting composition to the skin, mucous membranes, hair or scalp, wherein the composition comprises solid, polymorphic lipid particles which are crystalline or partially crystalline, optionally in the form of a solid inner phase (lipid phase) dispersed in an outer liquid phase, and wherein the solid polymorphic particles have an endothermic peak above 20° C. during the heating-up phase in heat calorimetry (DSC—differential scanning calorimetry) and have a size (average value of the main population) in the range of 10 nm to 1000 nm, and wherein the polymorphic particles comprise at least one selected from the group consisting of natural and synthetic mono-, di-und triglycerides, their mixtures, fatty alcohols, ethers of the same, individually or in a mixture, cetyl palmitate, glycerol monostearate, glycerol palmitostearate, glycerol ricinoleate, glycerol tribehenate (Compritol) gly-cerol trilaurate, hard fat (Witepsols), microcrystalline triglycerides (Dynasanes), and stearyl alcohol, individually or in a mixture.

30. Method according to claim 29, wherein the particles dispersed in an outer phase are applied directly as a dispersion onto the skin or mucous membranes.

31. Composition according to claim 2, comprising at least one molecular UV blocker selected from the group consisting of benzophenone and its derivatives, 4-phenylbenzophenone, 2-hydroxy-4-n-octyloxy-benzophenone, 2-hydroxy-4-methoxy-benzophe-none, 2,2'-dihydroxy-4,4=-dimethoxybenzophenone, suliso-benzone, benzimidazole derivatives, phenyl-benzimidazole sulfonic acid, camphor derivatives, 3-benzylidenecamphor, 3-(4-methylbenzylideneycamphor, terephthalylidenedicamphor sulfonic acid, dibenzoylmethanes, 4-isopropyl-dibenzoyl-methane, 4-tert-butyl-4'-methoxy-dibenzoylmethane, cinnamic acid esters, p-methoxycinnamic acid-2-ethylhexyl ester, p-methoxy-cinnamic acid isoamyl ester, p-methoxycinnamic acid octyl ester, p-methoxycinnamic acid propyl ester, p-aminobenzoic acid (PABA) and its derivatives, p-aminobenzoic acid glycerol ester, butyl-PABA, octyl-dimethyl-PABA, 2-ethylhexyl salicylate, homosalate, Mexoryl7 SX, Mexoryl7 XL, octylsalicylate, octyltriazone, and oxybenzone.

32. Composition according to claim 17, wherein the grinding comprises using at least one selected from the group consisting of ball milling, mortar milling and air-jet milling.

33. Composition according to claim 19, herein the lipid has been dispersed in an outer phase below its melting point using at least one selected from the group consisting of a rotor-stator colloid mill, a high-speed mixer, a dissolver disk, a high pressure homogenizer, a piston-gap homogenizer, and a Microfluidizer.

34. Composition according to claim 20, wherein the lipid has been dispersed in an outer phase close to or above its melting point using at least one selected from the group consisting of a rotor-stator colloid mill, a high-speed mixer, an Ultra-Turrax, Silverson mixer, a dissolver disc, a microscale or macroscale static mixer, a high pressure homogenizer, a piston-gap homogenizer and a Microfluidizer.

35. Composition according to claim 26, wherein the additional UV blocking substance and/or UV blocking particle is selected from the group consisting of particular titanium dioxide, zinc oxide, melanin, silicates, and Aerosils.

36. Composition according to claim 27, wherein it is present in the form of a lotion, cream, ointment, paste, stick, lipstick, or skin spray.

37. Composition according to claim 28, wherein t is present in the form of a shampoo, conditioner or aqueous or oily lotion.

38. Method according to claim 29, wherein the particles dispersed in an outer phase comprising water and applied directly as a dispersion onto the skin or mucous membranes.

39. Method of making a UV-protection composition comprising:

dispersing solid, polymorphic lipid particles in a medium, wherein the lipid particles that are crystalline or partially crystalline, optionally in the form of a solid inner phase (lipid phase) dispersed in an outer liquid phase, wherein the solid polymorphic particles have an endothermic peak above 20° C. during the heating-up phase in heat calorimetry (DSC—differential scanning calorimetry) and have a size (average value of the main population) in the range of 10 nm to 1000 nm, and wherein the polymorphic particles comprise at least one selected from the group consisting of natural and synthetic mono-, di- und triglycerides, their mixtures, fatty alcohols, ethers of the same, individually or in a mixture, cetyl palmitate, glycerol monostearate, glycerol palmitostearate, glycerol ricinoleate, glycerol tribehenate (Compritol), gly-cerol trilaurate, hard fat (Witepsols), microcrystalline triglycerides (Dynasanes), and stearyl alcohol, individually or in a mixture.

40. Method according to claim 39, wherein the lipid particles are dispersed in an outer phase below its melting point using at least one selected from the group consisting of a rotor-stator colloid mill, a high-speed mixer, in particular a dissolver disk, a high pressure homogenizer, a piston-gap homogenizer and a Microfluidizer.

41. Method according to claim 39, wherein the lipid particles are dispersed in an outer phase below close to or above its melting point using at least one selected from the group consisting of a rotor-stator colloid mill, a high-speed mixer, in particular a dissolver disk, a high pressure homogenizer, a piston-gap homogenizer and a Microfluidizer.

* * * * *